United States Patent
Auton et al.

(10) Patent No.: US 6,816,259 B1
(45) Date of Patent: Nov. 9, 2004

(54) METHOD AND APPARATUS FOR AUTOMATED EXCISION OF SAMPLES FROM TWO-DIMENSIONAL ELECTROPHORESIS GELS

(76) Inventors: Kevin Auton, 42 Croftfield Rd., Godmanchester, Huntingdon, Cambridgeshire, PE29 2ED (GB); Paul Thomas Ryan, 74 Owl End Gt. Stukeley, Huntingdon, Cambridgeshire PE17 5AQ (GB); David Byatt, 26 The Paddock, Eaton Ford, St. Neots, Cambridgeshire PE19 35A (GB)

(*) Notice: Subject to any disclaimer, the term of this patent is extended or adjusted under 35 U.S.C. 154(b) by 0 days.

(21) Appl. No.: 09/913,425
(22) PCT Filed: Feb. 17, 2000
(86) PCT No.: PCT/GB00/00573
§ 371 (c)(1), (2), (4) Date: Jan. 17, 2002
(87) PCT Pub. No.: WO00/49397
PCT Pub. Date: Aug. 24, 2000

Related U.S. Application Data
(60) Provisional application No. 60/120,471, filed on Feb. 17, 1999.

(51) Int. Cl.[7] .......... G01N 21/00; G01N 27/26
(52) U.S. Cl. .......... 356/344; 204/456
(58) Field of Search .......... 356/344; 204/456, 204/457, 466, 481, 606, 616; 382/129

(56) References Cited

U.S. PATENT DOCUMENTS

| 4,684,244 A | 8/1987 | Butts et al. |
| 4,909,920 A | * 3/1990 | Sarrine et al. .......... 204/457 |
| 6,064,754 A | 5/2000 | Parekh et al. |

FOREIGN PATENT DOCUMENTS

| WO | WO 98/23950 | 6/1998 |
| WO | WO 98/59092 | 12/1998 |

* cited by examiner

*Primary Examiner*—Alan Mathews
(74) *Attorney, Agent, or Firm*—Rader, Fishman & Grauer PLLC

(57) ABSTRACT

A system for automated excision of one or more samples from a sample media, including by using a device for electronically capturing one or more traits of samples in the media, using a microprocessor linked to the device to analyze the captured traits by comparison to reference databases, identifying samples of interest at location coordinates in the sample media, and automatically excising and processing the samples through the use of a novel robotic excision tool.

62 Claims, 13 Drawing Sheets

METHOD AND APPARATUS FOR AUTOMATED EXCISION OF SAMPLES FROM TWO-DIMENSIONAL ELECTROPHORESIS GELS

CROSS-REFERENCE TO RELATED APPLICATION

This application claims priority based on U.S. provisional patent application No. 60/120,471 filed Feb. 17, 1999.

FIELD OF THE INVENTION

The present invention relates to the analysis and separation of biomolecules. More particularly, the present invention relates to a method and apparatus for the automated excision of individual protein samples from two-dimensional electrophoresis gels for subsequent analysis of protein content.

BACKGROUND OF THE INVENTION

The method and apparatus described herein are used for the automated excision of individual samples from two-dimensional ("2D") electrophoresis gels for subsequent analysis (referred to herein as the "Invention"). The Invention may be used in any art or occupation where the user wishes to separate and analyze proteins or other substances that are identifiable by 2D gel electrophoresis techniques, or any other technique that results in the physical separation of substances within planar and cuttable materials.

By way of example, one such art is "proteomics," especially in conjunction with a related art, "genomics." Proteomics is the study of the protein complement that an organism is capable of producing, whereas genomics is the study of deoxyribonucleic acid ("DNA"), its genes, and the processes that lead to the creation of proteins. Proteomics provides data on the outcome of gene expression. Genomics provides the comprehensive gene sequence data, often derived by microarray analysis, required to advance protein research.

In complex organisms, individual cells may selectively express genes in their DNA to yield sets of proteins required for specific cell or organ functions. Much current scientific effort is directed to creating databases concerning how these genes are regulated and how this regulation may change in disease or other states, whether before and after treatment.

In order to evaluate the effects of gene regulation, methods must be used that measure, separate, and qualitatively and quantitatively analyze proteins, which are one output of gene expression. One currently favored protcomic technique is 2D polyacrylamide gel electrophoresis. This technique separates complex mixtures of proteins so that they can be isolated, quantified, identified and then assessed for their role in a disease process or as a target for novel drugs.

One approach to proteomic study using 2D gel techniques can be considered as comprising eight individual operations (see FIG. 1):

1. Solubilization 16—The proteins in a sample 15 of cells or tissue are released from the underlying cellular or tissue matrix by solubilizing the proteins with detergents.

2. Separation 17—The solubilized proteins are then physically separated into a square gel array using 2D gel electrophoresis.

3. Staining 18—The separated proteins are demonstrated in the gel by staining with or attaching Coomassie brilliant blue, silver staining, SYPRO ruby, fluorescent compounds, or by other appropriate techniques.

4. Imaging 19—The stained 2D gels are imaged by electronic optical or other means for resolving protein sample spots which are potentially interesting. For example, proteins that occur differentially in diseased but not healthy tissue could be considered of interest.

5. Picking 20—The spots of gel containing the proteins of interest are excised from the main gel matrix.

6. Digestion of protein into peptides 21—The proteins are broken down, usually enzymatically, into constituent peptides whose masses can be measured by mass spectrometry.

7. Mass spectral analysis 22—The size of the isolated and digested protein peptides are measured using a matrix assisted laser desorption ionization-time of flight ("MALDI-TOF") mass spectrometer, or analyzed by liquid chromatography-mass spectrometry, quadropole time of flight, or other means.

8. Identification 23, 24—The proteins are identified by matching the masses of the set of peptide fragments to fragments predicted by public and private databases after similar proteolytic (enzymatic) treatment. Once identified, the role of each protein in a disease process or as a potential point of intervention in a disease process (e.g., a drug target) can be considered along with information from pathology, pharmacology and known biological pathways.

In conjunction with computer databases and analysis, 2D gel electrophoresis can provide a means to physically resolve the proteome of a tested sample according to each protein's isoelectric point, reflected on one axis of the planar 2D gel sample, and its molecular weight or size, reflected by a corresponding perpendicular planar axis. Thus, 2D gel analysis of any given sample may produce a "fingerprint" that reflects an orthogonal planar distribution of its protein complement according to individual protein characteristics. Once prepared, resolved 2D gels may be translated by staining, imaging, and bioinformatic software into high-resolution digital protein maps, which may be stored for future use in computer or other databases. The resulting data may be used to determine the protein profiles of different tissues in both healthy and disease states, and ultimately for proteome libraries.

In addition, individual proteins may be excised from 2D gels, split into peptide fragments, and measured using mass spectrometry or other means. However, the large-scale study of proteins and protein networks is currently limited in part by the ability to physically isolate, segregate, and study individual proteins. Currently operations like those in FIG. 1 are done in a sequential and modular fashion. The output of each step is transferred manually from operation to operation. These individual unconnected manual operations make the technique slow and cumbersome, prone to error due to the repetitive nature of each manual step, and subject to contamination, for example, by keratin contamination from skin during handling.

Scientists studying proteomics and genomics, and others, are extremely interested in rapid, accurate high throughput methods and instruments to carry out protein analysis. It is clear that advances in robotics and software/computing technology could improve the throughput and rate of the analysis.

One U.S. company, BioRad Laboratories, is developing a protein-picking system in collaboration with a company called AARM (an Australian firm). However, among other distinctions, their system is only semi-automated, and the user must manually identify the proteins to be picked from a particular 2D gel. Furthermore, the BioRad system does not use information stored in 2D gel databases to identify proteins of interest to be excised. Finally, the BioRad system does not have the capability of utilizing excision tools of different sizes based upon the size of the protein in the 2D gel.

Although there is other information to suggest other interest in the field, see e.g., Anderson, et at., U.S. Pat. No. 5,993,627 at Columns 26–28, there appears to be no claimed invention or art providing the novel elements, means and utility of the claimed Invention.

SUMMARY OF THE INVENTION

The Invention offers a method and automated apparatus for the separation, excision, and high throughput handling of protein samples demonstrated via 2D gel for further analysis. The Invention utilizes a laboratory-grade XYZ Gantry robot, a novel approach to the identification of the proteins of interest to be excised, novel tools for the excision of the protein samples from the 2D gels, and novel means for controlling robot and process steps to accomplish selective and automated protein sample excision.

Currently, the process of protein excision is performed by hand, is extremely labor-intensive, and is prone to error. The manual process is also susceptible to contamination, rendering the protein under analysis virtually useless. The use of the laboratory robot and the novel excision tools described herein will increase the efficiency of protein excision and will greatly reduce contamination by minimizing user handling of the protein samples.

BRIEF DESCRIPTION OF THE DRAWINGS

The features and inventive aspects of the present Invention will become more apparent upon reading the following detailed description, claims, and drawings, of which the following is a brief description:

DETAILED DESCRIPTION OF A PREFERRED EMBODIMENT

Figure 1:
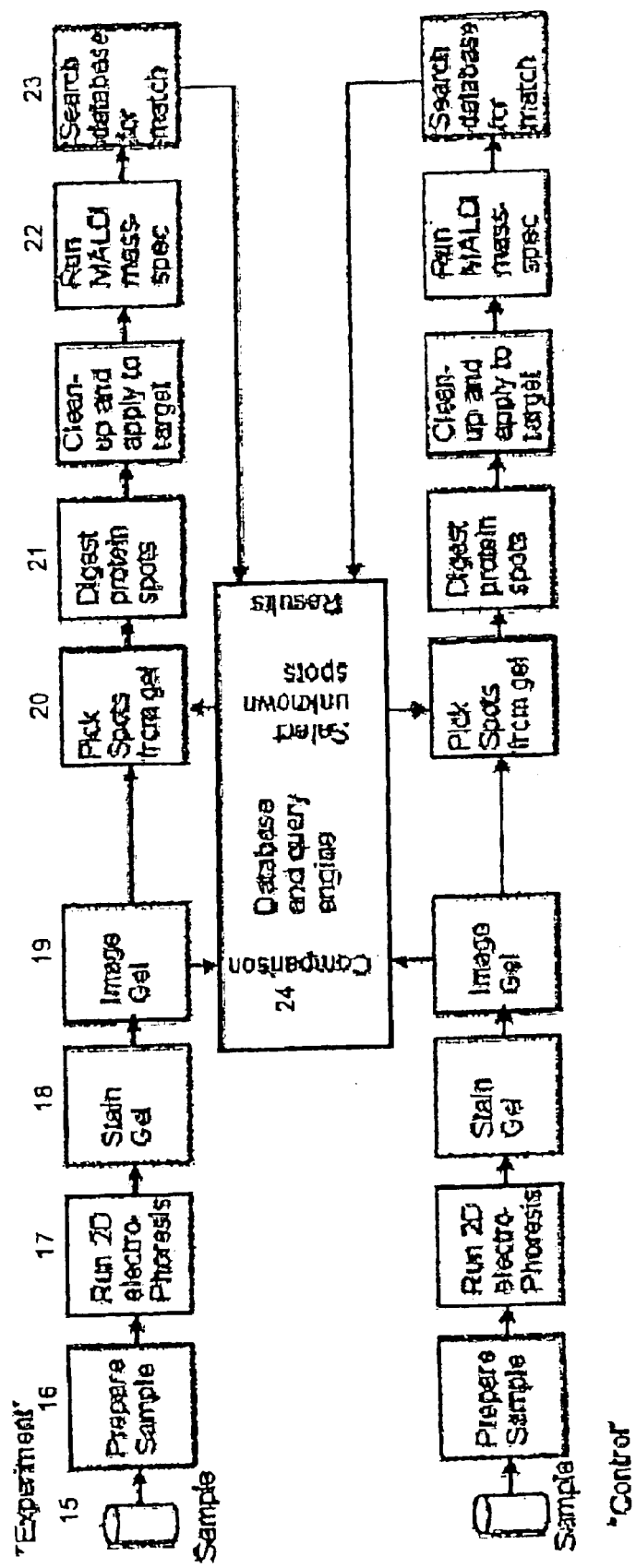
FIG. 1 is a logic flow diagram of one approach to proteomic analysis starting with a test or control sample and continuing through intermediate steps to data capture and analysis.

The basic process and elements of the Invention are to acquire an image of a processed 2D gel sample using a CCD or other camera or imaging system, analyze the image to find regions of interest arid to generate a "pick" list of spot coordinates, sample the selected gel regions by coring a gel plug from each of them, and deposit the core plug into a collection vessel. Steps in this process may include:

Presenting 2D gels 30, 38 to the excision working area of the machine

Presenting collection trays 40 for holding sample cores to the working area of the machine Presenting coring tips 42 and/or tray caps to the machine Illuminating the gel via a transmissive, reflective, visible, or ultraviolet light source Obtaining and capturing an electronic image of the gel by means of a mounted camera 28

Processing the image by computer means 26 to find contrasting areas, for example, by commercially available software Further electronic processing to identify protein spot areas of interest Further processing to calibrate geometry of the gel sample and any stored image Further processing to compare/contrast with database User processing to identify sampling positions Generating a list of physical positions to pick from and to link with calibrated identification information For each pick,
 Optionally collecting a new (clean) coring tool or clean the (reusable) tool
 moving the picking tool 29, 37 to the required position over the gel
 operating the picking tool to remove a core
 moving the core to the relevant well 79 in the output tray 40, 41
 depositing the core in a well 79
 disposing of coring tool (if disposable)
 collecting cap 77 from storage area, move to well 79
 capping the well
 Removing the output tray 88, 91 and gel from the machine at an appropriate time
 Downloading a log of picking information to another system to build the results into the (or another) database.

Gel images are usually captured initially by using an imaging system 28 and analyzing the image quantitatively with a commercially available, comprehensive 2-D gel analysis software package, such as Genomic Solutions, Inc.'s Investigator™ 2-D Analyzer Software. The image acquisition hardware provides high accuracy and high resolution and may offer special features to image fluorescent-or radioactive-marked gels.

Once a gel 30, 38 has been imaged and its data added to a database along with data from other gel samples, the gel may be stored for later processing. However, there may be distortion and movement of the gel during storage. If the distortion is not excessive, then the coring can be performed, relative to mechanical registration features on the gel carrier sheet. However, if the distortion is not acceptable, it must be corrected or accounted for prior to picking.

In one embodiment, the Invention may re-image the gel in the picking system to enhance basic accuracy and resolution. The image is then matched to the original stored image within the 2-D analysis software, and calibration factors are derived to match the spot coordinates in the original image with the actual gel sample for spot excision purposes.

The software allows users to optimize automatic spot finding with adjustable parameters. Users may perform database queries to filter information based on existence of spots, quantitative ratios of matched spots, spot integrated intensities, molecular weight, iso-electric point, area, and user-defined spot or image characteristics. The current system creates an image from the gel on the protein-picking robot. This image is subsequently "matched" with an image of the same gel analyzed previously. The process involves some user interaction to effectively "teach" the gel analysis software where to find the gel's "anchor points," which may establish a coordinate system for the gel under analysis.

The protein spots to be excised from the gel are identified via user-initiated queries to the spot image database via the 2-D software. For example, if the user desires to pick the proteins which have been overexpressed in an experimental schema with respect to a control sample, the user may initiate a database query to identify the spots and to relay their image coordinate positions to the picking robot.

Analytical software on the market already calculates the size of the spots, typically in square millimeters. The user or the software determines which spots are of interest, and the software creates a picking list with the coordinates of the spots within the image to be excised and the size of each spot. The pick list is created upstream from the picking process in a database of spots, taking individual images, and matching them together.

Optical calibration marks can be applied to the face of the gel carrier plate 31, 39, 77. These can be imaged by a high-performance imaging system, for example, the Investigator™ 2-D Analysis System, as well by lower performance cameras or imaging systems fitted to the picking system. Thus, the picking system can be used to re-image the gel sheet, and a match can be made to the "main" image, which was captured using a high-performance imager.

To further automate the protein picking process described herein, the Invention may use the incorporation of specific fluorophores to the proteins and specifically to the gel image anchor points. When excited by light of appropriate wavelength, the fluorophores incorporated into the gel's anchor points will emit light of a characteristic wavelength that can be imaged separately from the "study" proteins in the same gel. The anchor points are then imaged using an imaging system 28, such as a CCD camera or other imaging system, on the picking robot, and a segmentation algorithm will be applied to the digital image to determine the coordinates of the anchor points.

Alternatively, the additional reference marks may show contrast in both visible light and by fluorescence. Using such marks, the gel may be imaged first in a special fluorescent imaging system, separate from the picking system. Subsequently, the gel is imaged by a camera built into the picking system using visible-light contrast rather than fluorescent emission from the gel. This allows picking from gels stained by fluorophores even though the picking system is insensitive to the fluorescent emission. The two images (one from the separate fluorescent imaging system and the other from the camera built into the picking system) are matched using the reference marks since these are visible in both images. Once matched, the locations of desired (fluorescently marked) locations can be translated to the visible-light image and used as coordinates from which to pick.

Figure 3:
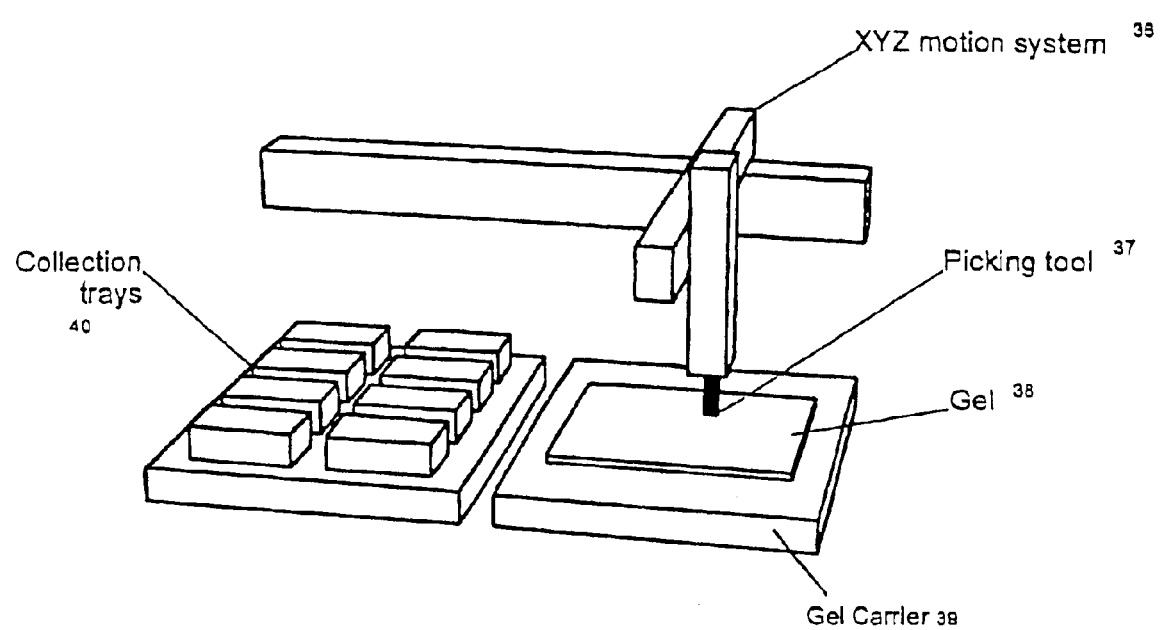
FIG. 3 is an illustration of positions of the robot arm, gel samples, and collection trays.

At the beginning of the picking cycle (FIG. 3), the operator mounts the gel on the gel carrier. 2D gels can be fragile and prone to tearing, creating some difficulty in transferring them from one substrate to another without damage or geometric distortion. In proteomic analysis, the registration of the gel must be maintained between imaging and picking in order to avoid degradation in accuracy. Because the imaging and picking may be done at different times and/or in different machines, it is important to be able to transfer the gel without distortion. This may be done by supporting the gel on a substrate that will not stretch and which has reference points that may be used in imaging and picking to ensure correct positioning. The present Invention may use a simple sheet of acrylic or silica glass, called a gel carrier sheet. The gel sheet is loose-laid onto a hard, smooth support. Alternatively, the gel may be fixed to a stretch-resistant substrate by, for example, proprietary materials such as "Gel Bond". Immobilizing the gel in this way eases the handling difficulties and reduces geometric distortion In the present embodiment, the gel carrier may be part of the robot, or an intermediate carrier that can be detached from the robot and used to transport the gel on the carrier. The gel carrier may be comprised of a fixture plate, a gel carrier, and a gel plate, all fitting on top of the other. The sheet can also have both mechanical and optical registration features. These are functionally transparent in order to permit transmission from the illumination source or have holes to permit transmission of light. Optionally, the substrate must also transmit UV light in order to allow UV illumination of gels marked with fluorescent dyes.

In any case, the light source can be fluorescent tubes or other suitable source. With the camera (or other imaging device) typically positioned above the gel, light may be passed upwards through the gel from beneath (transillumination) or shone downwards from above (epi-illumination). To aid spot finding by automatic processes, it is important that the illumination is maximally uniform. For transillumination, this is typically achieved with a diffusing grid or panel.

Figure 2:
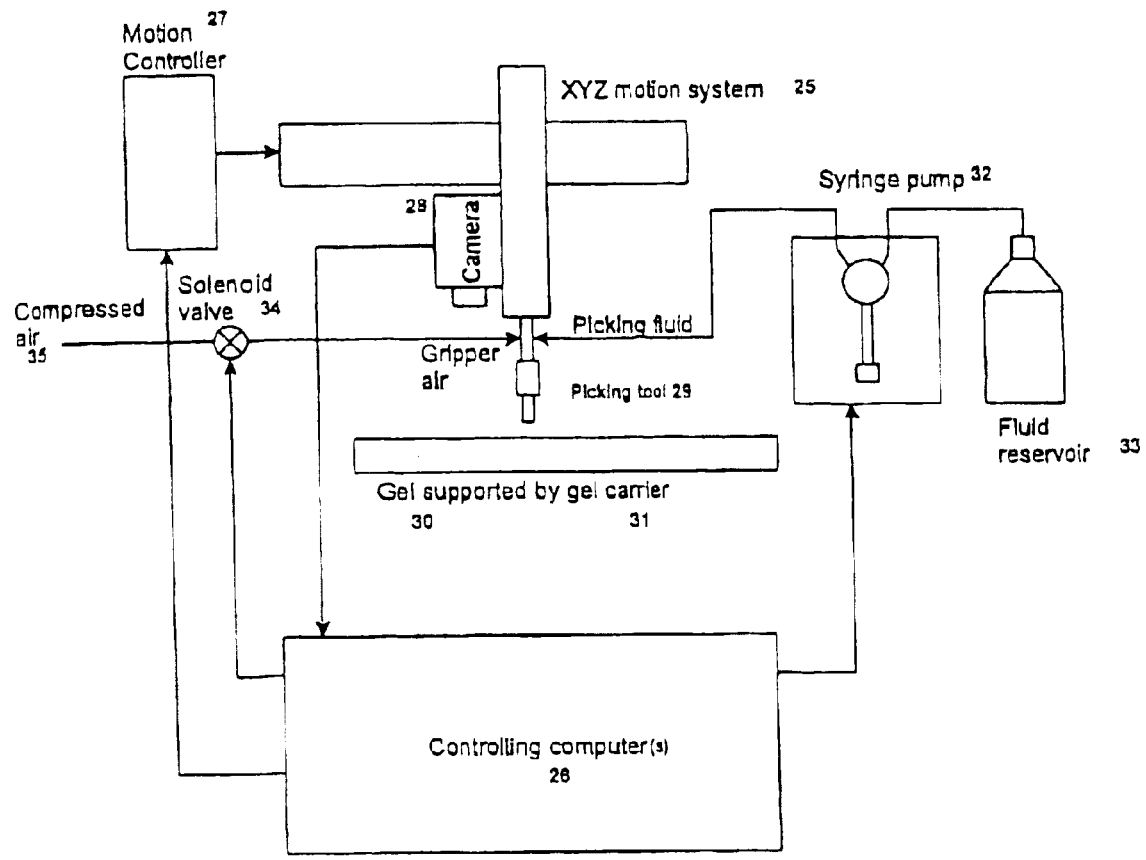
FIG. 2 is a schematic diagram of the basic elements of the current Invention.

The gel carrier is then transported to and mounted in the excision work area within the illumination zone. Once the gel has been placed in the carrier and moved to the sampling position, a camera may be used to determine protein spot locations in order to align the gel carrier's coordinate system with that of the previously analyzed image of the gel. In one embodiment, the camera is fixed to the moving head on the robot arm that can be used to image part of the gel (FIG. 2). The resulting images may be processed separately, or the individual "frames" from the camera image may be tiled to form a larger image. In another embodiment, the camera may be a high-resolution camera fixed above the gel, either above the head or not, in order to produce a single image.

When the images are obtained, the spots of interest are located by commercially available software in the controlling computer or in one or more other computers linked to the controlling computer 26. The analytical product gives XY coordinates for spot of interest for excision. Once the spots are found, certain picking criteria may be applied. By way of example, spot locations may be known to correspond with certain known proteins, or other spots found by comparison to images in the database may be selected for excision. The operator may employ different selection criteria using the images on the controlling computer or the associated computer and translated by means of operation of the computer back to the controlling arm. The communication contains one or more coordinates from which the computer will direct the arm to pick.

The controlling computer 26 (FIG. 2) performs a number of functions electronically, including controlling the motion commands 27 for the robot, executing tip pick-up and eject cycles, controlling the valves 34 to operate the feed of pressured gas or air, controlling solenoid valves 34 or syringe pump valves 32, and controlling the vacuum cycles and eject cycles for the samples themselves. Means for generating and implementing commands for such functions will be apparent to those skilled in the art. The controlling computer may be a single computer or a number of linked computers that intercommunicate so that individual tasks can be distributed 26. The camera on the robot may communicate with that computer, an additional computer, or an additional image processing system of other forms. The controlling computer may also communicate with another computer to control the automatic stacking and handling of plates or carriers (FIG. 13) in and out of the robotic system itself.

Mapping between image coordinates and robot coordinates is coordinated through a calibration procedure using a test target or targets. The coordinates are translated from stored spot image coordinates to robot coordinates by means of a mapping translation that performs a mathematical match between a test target position with known physical locations and coordinates from spot finding for that target. This is preferably part of the means in the controlling computer that controls the robot but may be embodied separately.

Figure 4:
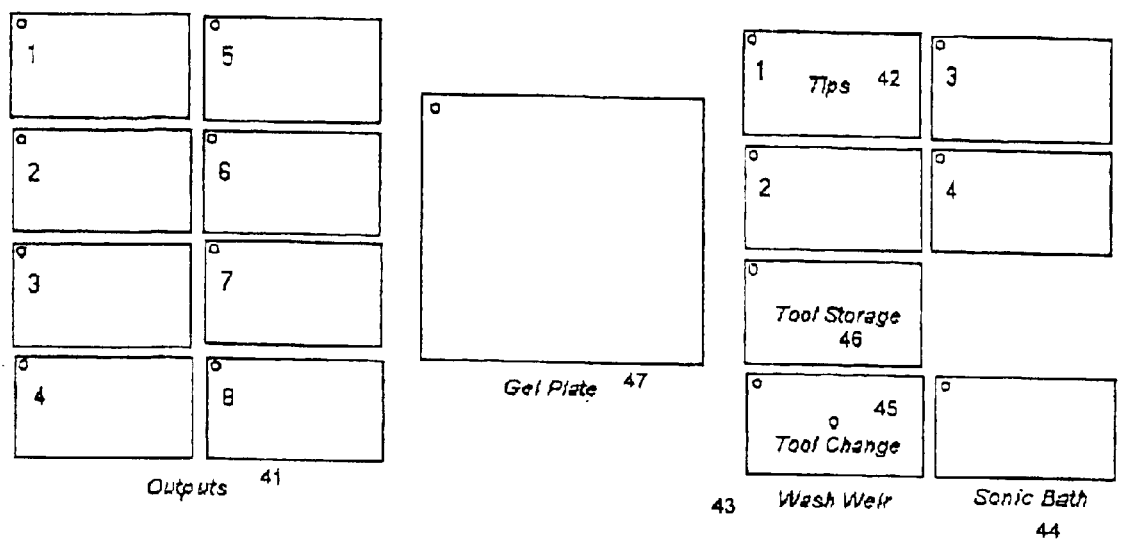
FIG. 4 is a top view of an arrangement of gel samples, tips, wash stations, and output trays, and related work areas.

Once picking coordinates have been established and communicated to the motion controller, the robot has a list of coordinates to pick from and may begin the picking cycle. The basic cycle takes the robot head to a drain position over a waste collection trough 43 (FIG. 4) 85. To achieve good performance, it is important to prevent cross contamination between successive coring operations. The target proteins are normally held within the gels, but should particles of gel be carried over from one coring operation to the next, then there is the potential for contamination. Fluid is discharged through the tip by cycling the syringe pump in order to wash out debris and to ensure that the system is filled with fluid. The fluid 33 used during the picking cycle must match that used during pretreatment of the gel so that mismatch in composition of the fluids does not cause shrinkage or expansion of the gel, Such fluids may be water, 10% ethanol/water, 10% ethanol/2% glycol/water, or other compatible fluids.

In one embodiment using an interchangeable tip, the tips are held in a separate rack 42, 84. At the beginning of a picking run, the robot picks up a tip. With interchangeable tips, the robot may be instructed to use one tip for the whole picking run, or to use a new tip for each picked spot during the picking run, putting the tip away and collecting a new one, for example, to reduce the possibility of cross-contamination among samples. Optionally the controlling computer may be programmed to direct a washing procedure so that each of the interchangeable tips are put through a washing procedure automatically in the absence of a gel, through optional water, other solvent or ultrasonic baths 43, 44, 83:

In a preferred embodiment, the gel may be irrigated during the picking. At a predetermined interval selected by the operator, the picking tool 29, 37 may begin an irrigation process comprised of moving the head back and forth across the gel in a raster fashion, dropping fluid as it proceeds. The patterns may repeat, change directions, or the wetting pattern may be shifted by a fraction of the line pitch, for example, to irrigate in the gaps between previous lines in order to enhance uniform irrigation. Excess fluid during irrigation runs off the gel onto the carrier plate 39 into a waste collection trough 85.

Figure 5:
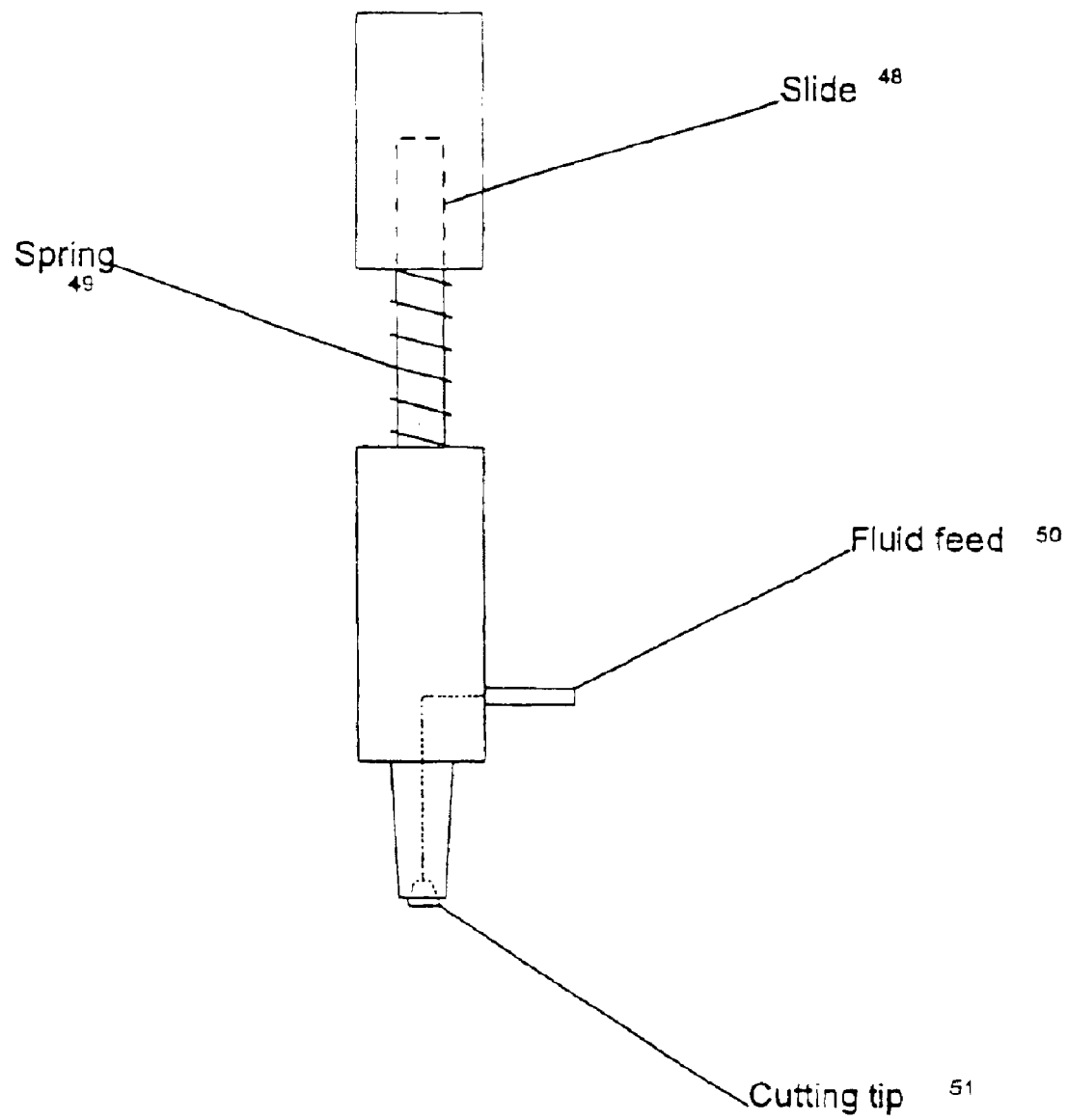
FIG. 5 is an illustration of a fixed cutting tool arm and tip.
Figure 6:
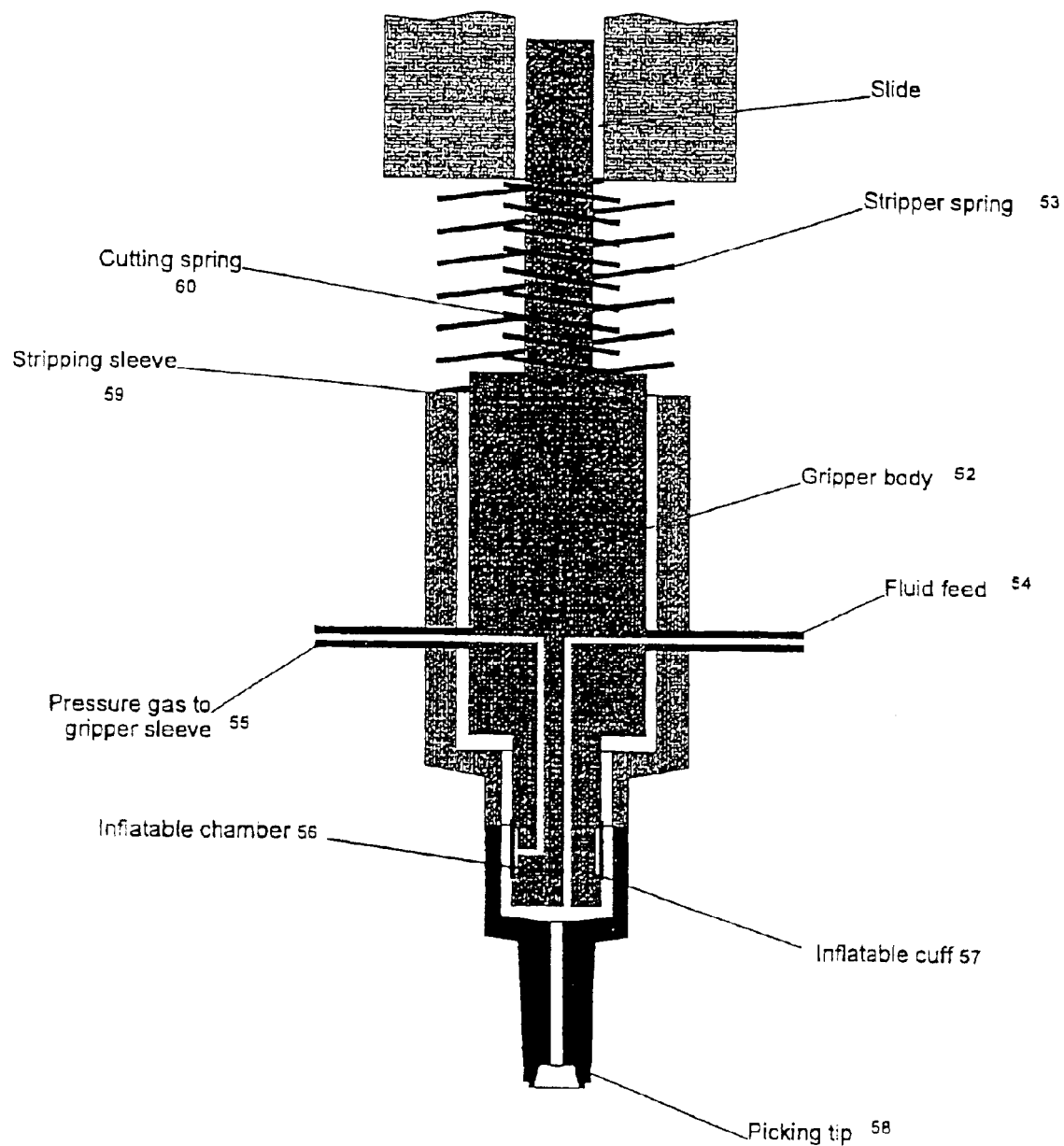
FIG. 6 is an illustration of a cutting tool arm and tip used with interchangeable or disposable tips.

The robot arm may be used with a fixed tip with a semipermanent connection (FIG. 5), or an interchangeable tip that may be disposable or reusable (FIG. 6). Fixed tips may be made of stainless steel or similar metal known to one skilled in the art that is low corrosion and high cleanliness, cleanable with corrosive solvents with no leeching from the materials. The interchangeable or disposable tips may be made of various polymers, such as polypropylene, nylon, or POM (acetal) materials, or other suitable materials.

To minimize contamination, the tip may be cleaned between coring operations or it may be replaced (i.e. a disposable coring tip). The latter approach is preferred for best performance. The tips may be of the same diameter, or different diameters may be selected according to different spot parameters, such as spot diameter or optical density.

A robotic manipulator 25 optionally carries a tool gripper. When interchangeable tips are used, the head gripper on the robot arm has means to grip, hold and eject the tips, an eject spring 53 with an associated sleeve 59, and an inflatable cuff 57 (FIG. 6). There are two feeds to the head gripper. One feed 54 provides fluid pressure or vacuum through the gripping tip to a picking tip from the syringe pump 32 and fluid reservoir 33 to enable gel core extraction and ejection. The gripper has a cylindrical elastic cuff 57 that can be expanded by internal gas or liquid pressure. The second feed 35, 55 supplies the cavity 56 between the inflatable cuff 57 and the body of the gripper 52. That cavity is inflated with air, other gas or fluid to push out the cuff to grip the internal wall of the tip. The cuff inflation pipe 55 communicates through the body of the gripper to the cavity 56 behind the inflatable cuff 57 for all interchangeable and disposal tips.

When no interchangeable tip is in place, the robot arm 25 with the gripper 52 may be cycled to the tip rack, moved so that gripper 52 inserts into the cavity of a tip 58, and lowered to depress the eject spring 53. Pressure is then applied to the inflatable cuff 57 so that it inflates and grips inside of the tip. The gripper is then withdrawn vertically with the tip in place. The eject spring 53 remains compressed due to the insertion into the cutting tip 58. After the gel coring operation has been performed, the cuff pressure may be released, thereby releasing the gripping pressure and permitting the eject spring (with a force, for example, of a range of ½–1 Newton) to eject the interchangeable tip. There is an intermediate sleeve 59 between the eject spring and the disposable or interchangeable tip to bear between the spring and the end of the tip.

With a fixed picking tip (FIG. 5), there are no inflatable cuffs; and the cutting edge 51 is built as part of the gripping tool with a single fluid way 50 and attached to the moving head of the robot with semi-permanent means.

Figure 8:
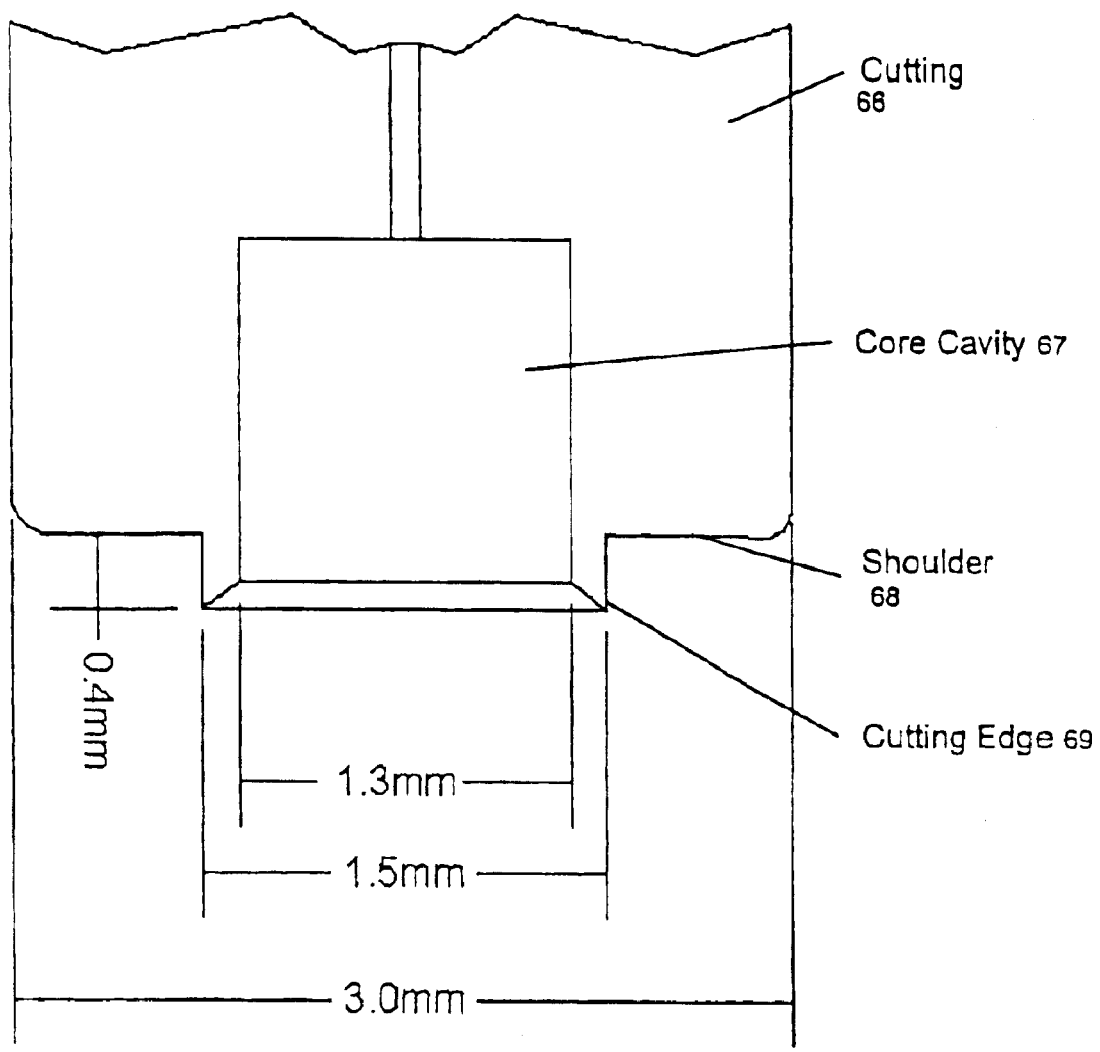
FIG. 8 is an illustration of the sample dimensions of a cutting tip with a configured shoulder setback.

There are variations in configuration and dimensions of the cutting tips. Simple trials on 1.5 mm gels suggest the preferred tip dimensions shown in FIG. 8. In one embodiment, the lead edge 69 of the cutting tip may have an inside diameter of 1.3 millimeters and an outside diameter of 1.5 millimeters, , with a shoulder 68 setback of 0.4 millimeters from the lead edge 69. The internal diameter of the cutting tip may range from 0.5 mm up to 5 mm, with a fine cutting edge width, for example about 0.1 mm width, and a sharpened and preferably beveled edge.

It would be beneficial to apply a radius to the outer corner of the shoulder 68 to minimize damage to the gel in the vicinity of the pick. The setback of the shoulder and the outer diameter of the outer shoulder may be varied according to the gel thickness and mechanical properties, such as elasticity, tear and tensile strength. The depth of the shoulder and the overall diameter may be optimized for a particular gel thickness and gel properties. The above referenced dimensions are typical cutting tip dimensions for use with 1 mm to 1.5 mm thickness duracryl gels. With a thicker gel, the 4 mm outside diameter and the shoulder setback are increased. For a weaker gel with a lower tensile strength for a given amount of elasticity, the cutting setback shoulder depth would be increased.

Figure 9:
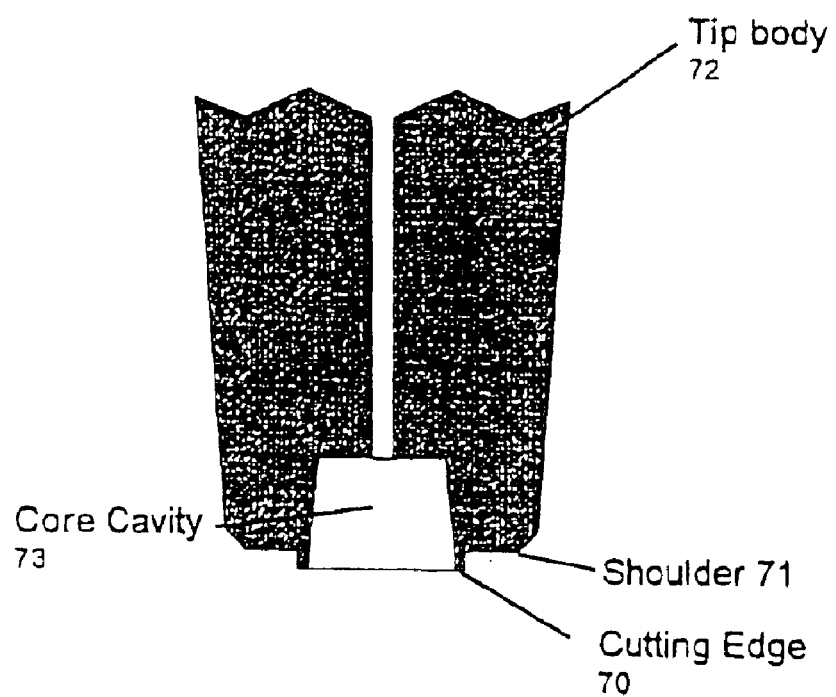
FIG. 9 is an illustration of a cutting tip with a shoulder setback and conical internal coring cavity.

In one preferred embodiment (FIG. 9), the internal shape of tip is optimally conical to create a tapered core cavity 73 to the tip. This improves reliability of ejection of gel plugs after picking. If the cavity is cylindrical, there is a possibility that during ejection by fluid pressure, the plug may twist in the cavity about an axis perpendicular to the axis of the tool. This creates an escape path for the ejection fluid and consequently the plug may not eject. This mode is similar to the action of a butterfly valve so is known as a "butterfly valve" failure. Making the internal cavity conical restricts the ability of the plug to rotate so improving reliability. The dimensions optimally include a 14-degree taper on each side of the cavity 73 beginning at the internal edge of the bevel. The internal tapered cavity may be polished to avoid gripping on any rough surface. The depth of the cavity is matched to the depth of the thickness of the gel, typically equal to the thickness of the gel.

Figure 10:
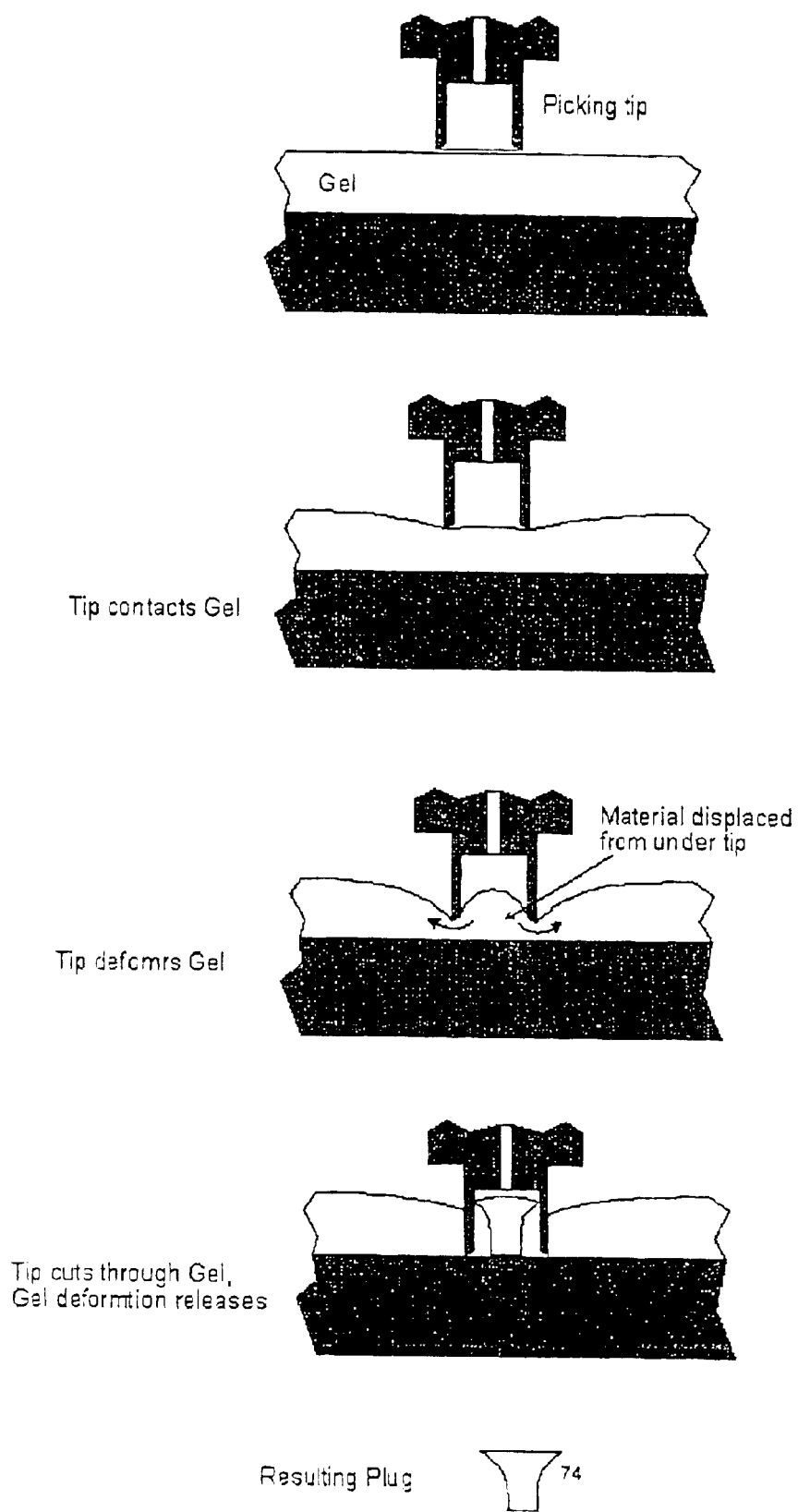
FIG. 10 is an illustration of sample plug cutting and shape using a cutting tip without a configured shoulder.

As a plug is cut, the gel may deform in such a way that the resulting plug shape is "mushroom"-shaped 74 (FIG. 10). This shape has two main effects: (1) during vacuum extraction, there is a tendency to ingest the plug into the body of the picking tip; and (2) the amount of material in the plug is substantially reduced, leading to a plug sample that is smaller yet material is still taken from a larger area, resulting in poorer sample/background ratio or overall resolution.

Figure 11:
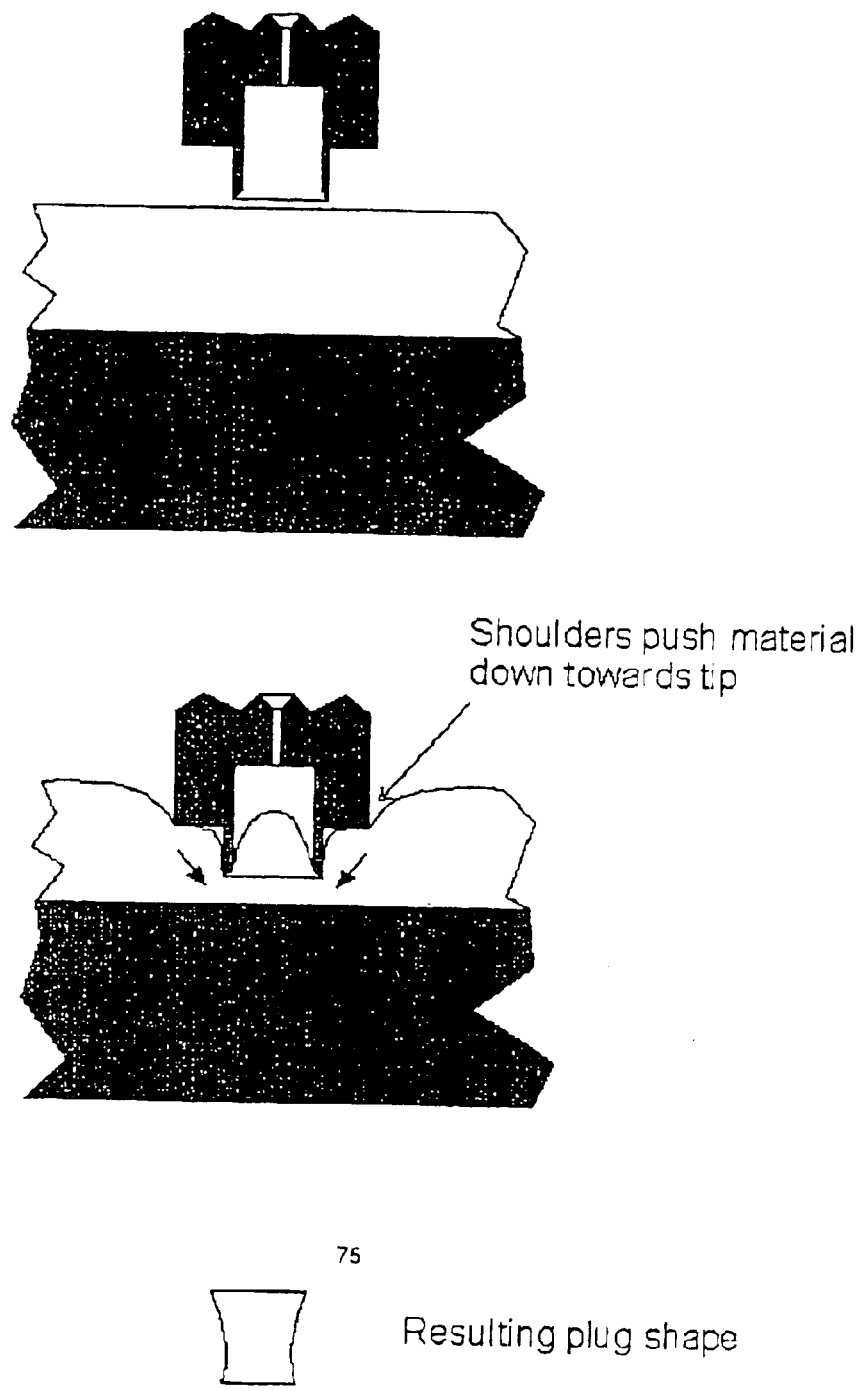
FIG. 11 is an illustration of sample plug cutting using a cutting tip with a configured shoulder.

The shoulder 71 on the cutting tip may be used to change the shape of the resulting core sample (FIG. 11). If one is less concerned about the shape of plug, or if one is cutting large sample plugs (in comparison to the thickness of the gel) where mushrooming is less significant, one need not use the shoulder. In other circumstances, the shoulder tends to push material back under the tip to counteract the distortion caused by the cutting force. Shoulder depth and shoulder diameter are parameters that need to be set to match a given gel thickness, stiffness and cutting strength. The match is not critical, however, as variances result in relatively small changes in plug shape.

In the preferred embodiment, this sample shape is addressed by producing "conical" plugs 75 (FIG. 11). The degree of "conicality" depends upon the ratio of tip diameter to gel thickness and the cutting force relative to the gel stiffness. The cutting force is a function of cutting perimeter, edge sharpness and gel properties. In practice, a conicality ratio of around 2:1(max diameter to min diameter) is common.

As the picking cycle continues, the tip is purged at the waste collection trough 43, 85, with fluid cycled through it from the fluid reservoir 33 using the syringe pump 32 to ensure that the tip is clean and that the system is purged of air with a full complement of fluid. The robot then is commanded to the X-Y position on the gel and spaced off the gel by a small distance, such as 5 mm. Optionally, a small amount of fluid, such as 40 microliters, is dispensed from the picking tip onto the gel in a prewetting step so that the picking target is prewetted.

Figure 7:
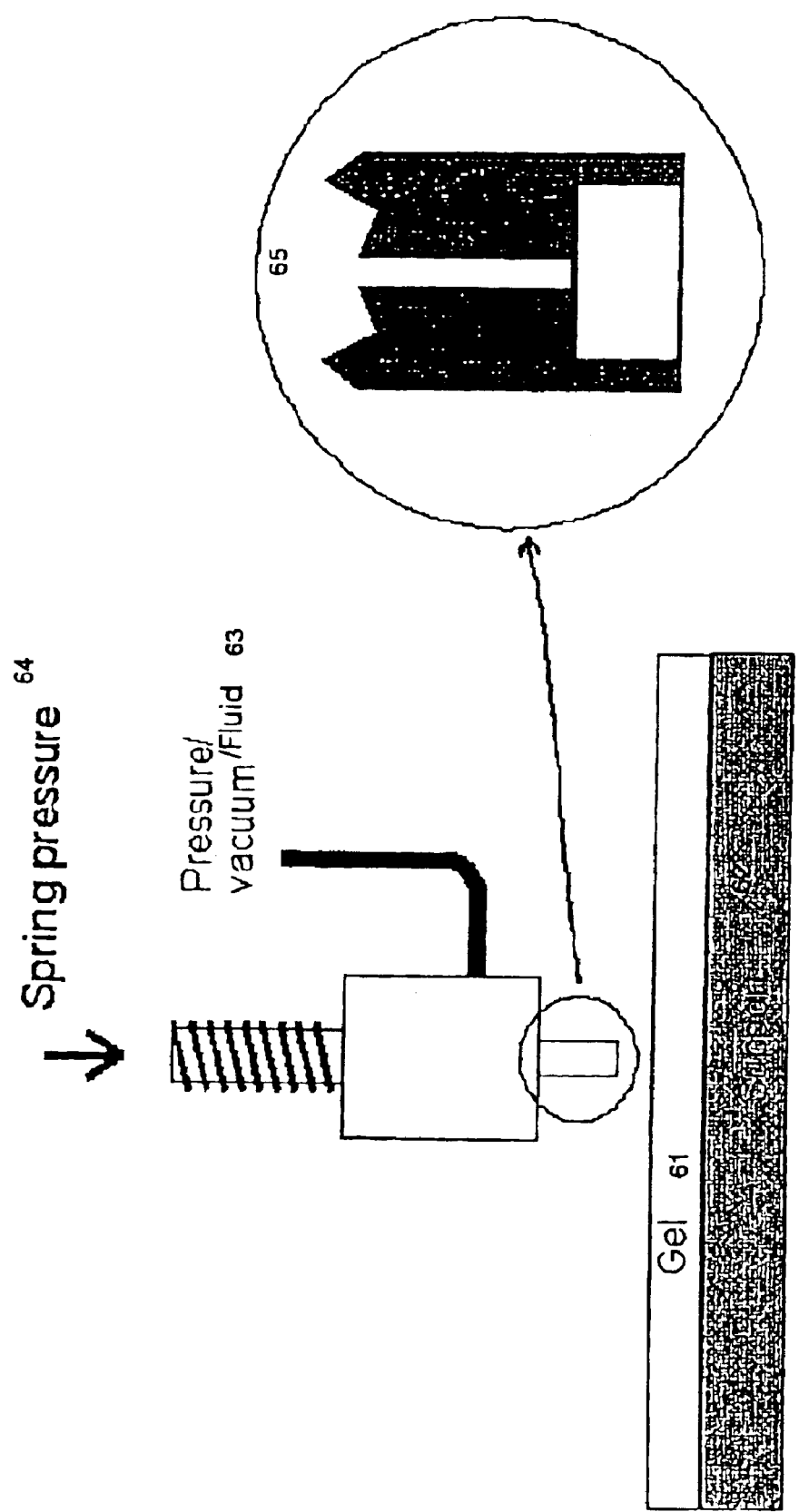
FIG. 7 is an illustration of an example of a configuration for a gel picking run.

Air is then aspirated back into the tip to form an air lock volume, such as 100 ul. The picking tip is lowered onto the gel until the spring 60 supporting the picking tip compresses, defining the cutting force 64 and cutting through the gel to the hard gel support (FIG. 7). The cutting tool has a hollow cutting tip 65 of selected size and shape that is pressed down through the gel sheet until it meets the supporting sheet (FIG. 7). The tip may be spring-loaded to limit the insertion force and to accommodate inaccuracies in the vertical registration of the tool to the supporting sheet. A preferred spring force is approximately 3 newtons.

The syringe pump 32 is then operated in suction mode to withdraw a small volume of fluid, such as approximately 70 microliters, forming a partial vacuum that is applied through the feed line into the picking tip that has been sealed by insertion into the gel. The aspirated air acts like a spring to control the amount of vacuum applied to the plug. This aspirated airlock also acts to separate the contaminated zone in the coring tool, preventing gel particles or other contaminants from being taken up into the gripper or the feed tube. It is important that the airlock is not too large as this increases the ejection compliance that can hinder placement of the core in the well. A small compliance is, however, advantageous during core extraction as it helps maintain a partial vacuum (as the core is taken from the gel sheet) if there is a small leak around the core in the tip.

To remove the core, the tool is withdrawn, taking the gel plug with it. However, the softness and wet state of the sheet may cause problems. Firstly, as the tool presses in, the gel under the cutting edge distorts and tends to move outwards (away from the axis of the tool). A second problem also relates to removal; as the tool is pulled out, a vacuum develops under the tip. This is not relieved as the wetness of the sheet maintains a good seal and the result may be that the core is left in the sheet. The Invention addresses these issues by:

As discussed above, by applying vacuum to the top of the gel plug via the tool to hold the core in the tool Optionally, once the core has been cut, by moving the tool laterally for small distances (for example, ½ mm) before removing it from the sheet. This overcomes any gel adherence to the underlying carrier and breaks any vacuum that may exist between the plug and the gel itself by opening a small gap between the outside of the tool and the remainder of the sheet to allow air (or free fluid) under the edge of the tool.

Figure 12:
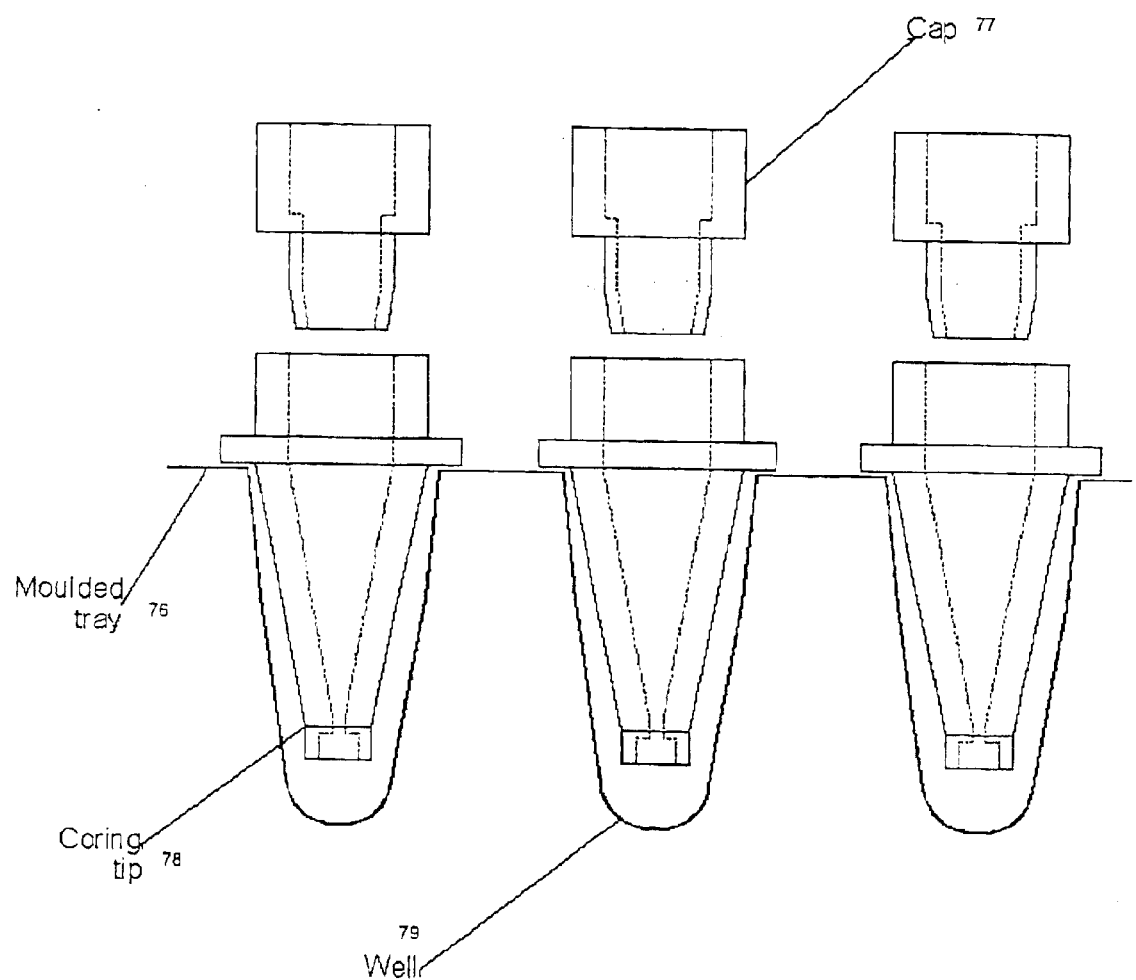
FIG. 12 is an illustration of alternative tip or cap insertion into collecting tray wells.

The tip is then lifted out of the gel and transported with the cut plug to the collection tray 40, which is typically a ninety-six (96) well microtiter plate. Gel plugs are placed individually into small wells in the microtiter plates. The narrow portion of the picking tip is lowered partially into the well (FIG. 12). A small amount of fluid is dispensed via the syringe plug, ejecting the core sample. The fluid will include the air lock volume, plus the backoff volume, plus a small volume, such as a net 100 microliters, pushing the plug out of the cup in the end of the tip, capturing the plug in a droplet, and dropping the droplet off the tip into the well. Use of liquid in contrast to gas pressure to eject the plug reduces the ejection velocity, which can cause the ejected sample to bounce around within the collection vessel. Liquid ejection is a much slower, controlled process ensuring that the sample is deposited in the bottom of the well captured in fluid to keep it hydrated if the plate goes into storage. The plates may then be covered manually or automatically, with adhesive plates or otherwise fixed coverings (for example plastic sheet heat-sealed to the open tops.)

With interchangeable tips, the tip may be put down or disposed, and a cap that fits the gripper may be picked up and pushed into the collection tray with the spring, plugging the microtiter well (FIG. 12).

In one embodiment, the caps are fitted into the coring tips, and the resulting stacks placed in the wells. In the machine, the gripper first takes hold of the inner cap and lifts the cap and coring tip combination out of the tray. In this embodiment, the coring tip is used to extract a core from the gel and deposit it back into the vacant well in the tray. A stripping device is provided in the machine into which the used coring tip is inserted. This holds onto the coring tip, and the cap is pulled out of the coring tip by the gripper. A flange may facilitate this operation. The coring tip falls to waste from the stripping device, and the robotic manipulator replaces the cap into the tray well.

If the coring tips are made so their major bores match those of the tray wells, then the caps can be fitted either into the tray wells or into the coring tips. This allows both the caps and coring tips to be pre-loaded into the trays before the trays are presented to the machine. It will be evident that the cap must have a hole to allow pressure/vacuum to pass to the coring tip. This may permit subsequent stages of processing where it is necessary to insert a probe into the well, such as to permit protein digestion. The hole in the cap is made to match the dimensions of the probe to provide the partial seal around the probe necessary for the particular fluid handling. The robot cycles to pick up a new tip, to perform another wash bath cycle and then the next cycle is started.

Figure 13:
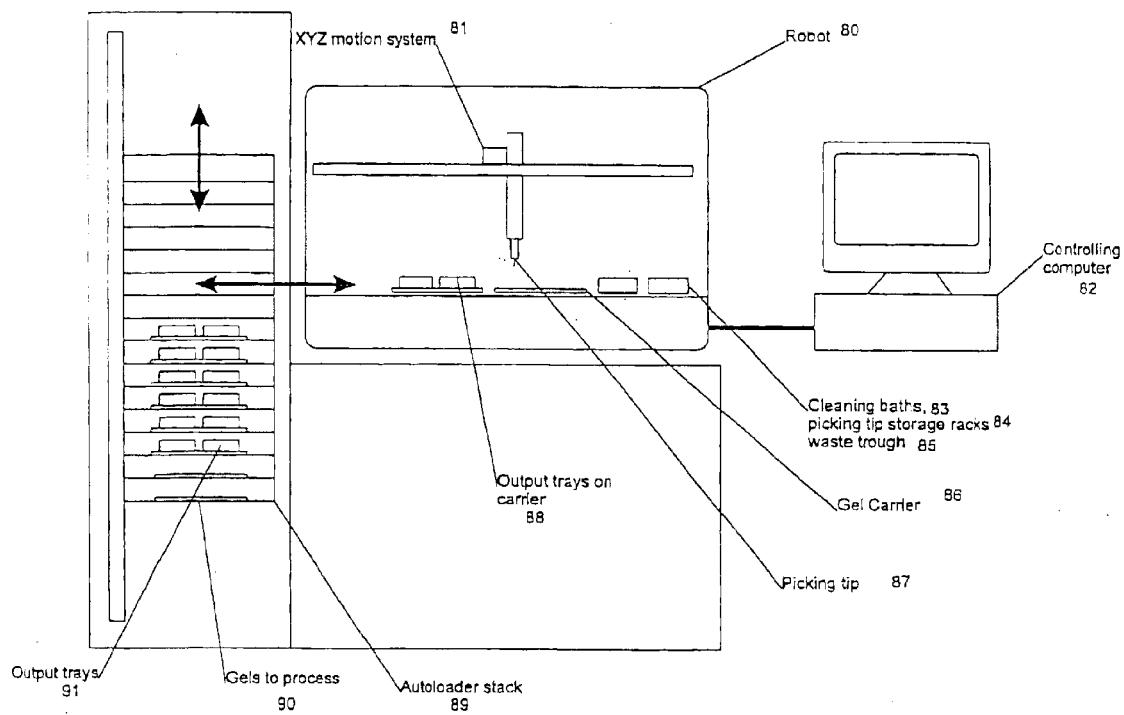
FIG. 13 is an illustration of automated means to transport and handle pluralities of gel samples and collecting trays.

One embodiment may include an autoloader, thus permitting several picking runs to be performed (FIG. 13). Once spots are picked from a gel, the gel may be shunted off the bed of the machine into an automatic stacker 89, and the next gel is placed on the machine for picking. The existing output tray 88 may continue to be filled, or additional output trays 91 may be loaded to match trays with gels. The gel carrier 86 moves back and forth in the stacking system. Each gel would have a removable lid that would be automatically removed before the gel is placed on the robot. A separate part of the stacking system takes the carrier out of the stack, removes the lid, optionally retaining the lid or placing it back in the stack, and then places the carrier with the exposed gel on the bed of the robot (optionally via a vacant position in the stack). Vertical stacks of pigeonholes take gel carrier or sets of output plates for automatic dispersal.

Preferred embodiments of the present Invention have been disclosed. A person of ordinary skill in the art would realize, however, that certain modifications would come within the teachings of this invention, and the following claims should be studied to determine the true scope and content of the invention. In addition, the methods and structures of the present invention can be incorporated in the form of a variety of embodiments, only a few of which are described herein. It will be apparent to the artisan that other embodiments exist that do not depart from the spirit of the invention. Thus, the described embodiments are illustrative and should not be construed as restrictive.

What is claimed is:

1. An apparatus for automated excision of one or more samples from a sample media, comprising:
   a. a device for electronically capturing one or more traits respectively associated with one or more samples present in a sample media, and
   b. a microprocessor linked to said device for analyzing one or more of said electronically captured traits of one or more of said samples, wherein said microprocessor accesses a database of reference traits and compares at least one electronically captured trait of at least one sample against one of said reference traits in said database of reference traits, wherein the microprocessor identifies one or more samples of interest as a result of comparing at least one of said electronically captured traits against one of said reference traits.

2. The apparatus of claim 1, further including a robotic excision tool coupled to said microprocessor, wherein said microprocessor commands said robotic excision tool to excise at least one sample of interest.

3. The apparatus of claim 2, wherein said microprocessor commands said robotic excision tool to irrigate said sample media with fluid from a fluid reservoir.

4. The apparatus of claim 2, wherein said robotic excision tool includes a plurality of excision cutters.

5. The apparatus of claim 4, wherein said microprocessor associates at least one said sample of interest with one of said plurality of excision cutters and commands said robotic excision tool to select one associated excision cutter for excision of the associated sample.

6. The apparatus of claim 2, wherein said microprocessor identifies location coordinates for said sample of interest in said sample media.

7. The apparatus of claim 6, wherein said microprocessor commands said robotic excision tool to excise said sample of interest at said coordinates.

8. The apparatus of claim 6, wherein said microprocessor identifies said location coordinates by deriving and applying calibration factors from comparison of one or more of said electronically captured traits with one or more of said reference traits.

9. The apparatus of claim 1, wherein said sample media includes a two-dimensional electrophoresis gel sample.

10. The apparatus of claim 1, further including an illuminating source for illuminating said sample media.

11. The apparatus of claim 1, wherein said device is a camera and wherein said trait is an optical trait.

12. The apparatus of claim 1, wherein said sample media is located on a substrate.

13. The apparatus of claim 12, wherein said substrate is a stretch-resistant substrate.

14. The apparatus of claim 12, wherein said substrate contains reference marks.

15. The apparatus of claim 1, wherein said sample media contains fluorophores.

16. The apparatus of claim 1, wherein one or more of said samples contains fluorophores.

17. The apparatus of claim 2, wherein said microprocessor commands said robotic excision tool to deposit said excised sample of interest into a sample receptacle.

18. The apparatus of claim 17, wherein said excised sample is deposited into said sample receptacle along with a volume of fluid from a fluid reservoir.

19. The apparatus of claim 17, wherein said microprocessor commands said robotic excision tool to excise and deposit a plurality of said samples of interest sequentially into a plurality of said sample receptacles.

20. The apparatus of claim 17, wherein said microprocessor commands said robotic excision tool to pick up and place a cap on said sample receptacle.

21. The apparatus of claim 17, where said robotic excision tool has means for sequentially processing a plurality of said sample media.

22. The apparatus of claim 17, wherein aid robotic excision tool has means for sequentially processing a plurality of said sample receptacles.

23. The apparatus of claim 2, wherein said robotic excision tool has an excision cutting tip containing a conical cavity.

24. The apparatus of claim 2, wherein said robotic excision tool has an excision cutting tip that bears a sharpened cutting edge.

25. The apparatus of claim 24, wherein said sharpened cutting edge is beveled.

26. The apparatus of claim 2, wherein said robotic excision tool has an excision cutting tip with a shoulder surface and a cutting edge, said shoulder being set back vertically from said cutting edge.

27. The apparatus of claim 2, wherein said robotic excision tool has an excision cutting tip that is fixed on said excision tool by semi-permanent means.

28. The apparatus of claim 2, wherein said robotic excision tool has an excision cutting tip that is interchangeable.

29. The apparatus of claim 28, wherein said robotic excision tool has means to grip and eject said interchangeable tip.

30. The apparatus of claim 28, wherein said robotic excision tool includes means for automatically disposing of said interchangeable tip.

31. The apparatus of claim 29, wherein said microprocessor commands said robotic excision tool to grip and eject said interchangeable tip.

32. The apparatus of claim 29, wherein said means to grip and eject said interchangeable tip includes a cylindrical inflatable cuff, an ejection spring, and means to control pressure to and from said inflatable cuff from pressure sources.

33. The apparatus of claim 32, wherein said pressure is fluid pressure.

34. The apparatus of claim 32, wherein said pressure is gas pressure.

35. The apparatus of claim 2, wherein said robotic excision tool has means to eject said excised sample of interest into a sample receptacle.

36. The apparatus of claim 35, wherein said means cycles and discharges fluid from a fluid reservoir through said robotic excision tool by means of a pump.

37. The apparatus of claim 36, wherein said microprocessor commands said pump to sequentially discharge, withdraw, or further discharge said fluid through said robotic excision tool.

38. The apparatus of claim 2, wherein said microprocessor commands said robotic excision tool to displace laterally after contact with said sample of interest.

39. A method for automating the excision of one or more samples from a sample media, comprising the steps of:
    a. capturing electronically one or more traits respectively associated with one or more samples present in a sample media,
    b. comparing one or more of said captured traits against a database of reference traits,
    c. as a result of step b), selecting a sample of interest from one or more samples present in said sample media,
    d. establishing reference coordinates of said sample of interest,
    e. associating a coring tool with said sample of interest, and
    f. automatically excising said sample of interest with said coring tool by reference to said coordinates.

40. The method of claim 39, further including the step of recapturing said one or more traits and comparing the captured traits against the recaptured traits to derive a calibration factor.

41. The method of claim 39, further including the step of mounting said sample media on a substrate that contains reference marks.

42. The method of claim 39, wherein said comparing of step b) includes comparing at least one of the following traits against a database of reference traits: quantitative ratios of match samples, sample integrated intensities, sample molecular weight, sample isoelectric point, sample area, or sample density.

43. The method of claim 39, further including the step of illuminating the sample media with ultraviolet light.

44. The method of claim 39, further including the steps of automatically disposing of the coring tool and selecting a new coring tool.

45. The method of claim 39, further including the step of automatically cleaning the coring tool.

46. The method of claim 39, wherein step e) further includes selecting a coring tool from a plurality of coring tools.

47. The method of claim 39, further including the step of depositing said excised sample of interest into a sample receptacle.

48. The method of claim 47, further including the step of automatically depositing a plurality of said excised samples of interest into a plurality of sample receptacles.

49. The method of claim 47, further including the step of ejecting said excised sample of interest by discharging fluid from a fluid reservoir associated with said coring tool into said sample receptacle.

50. The method of claim 39, further including the step of providing a coring tool with a conical coring cavity.

51. The method of claim 39, further including the step of providing a coring tool that is interchangeable.

52. The method of claim 51, further including the step of gripping said interchangeable coring tool through inflation of a cylindrical inflatable cuff inside the coring tool by liquid or gas pressure.

53. The method of claim 52, further including the step of ejecting said interchangeable tool by releasing said pressure inside said inflatable cuff and applying force to said interchangeable tool with an ejection spring.

54. The method of claim 39, further including the step of providing a sample media that is a two-dimensional gel electrophoresis sample.

55. An apparatus for automated excision of one or more samples from a sample media, comprising:
    a. a device for electronically capturing one or more traits respectively associated with one or more samples present in a sample media,
    b. a microprocessor linked to said device for analyzing one or more of said electronically captured traits of one or more of said samples, wherein said microprocessor accesses a database of reference traits and compares at least one electronically captured trait of at least one sample against one of said reference traits in said database of reference traits, wherein the microprocessor identifies one or more samples of interest as a result of comparing at least one of said electronically captured traits against one of said reference traits, and
    c. a robotic excision tool coupled to said microprocessor, wherein said microprocessor commands said robotic excision tool to excise at least one sample of interest.

56. An apparatus for automated excision of one or more samples from a sample media, comprising:
    a. a device for electronically capturing one or more traits respectively associated with one or more samples present in a sample media,
    b. a microprocessor linked to said device for analyzing one or more of said electronically captured traits of one or more of said samples, wherein said microprocessor accesses a database of reference traits and compares at least one electronically captured trait of at least one sample against one of said reference traits in said database of reference traits, wherein the microprocessor identifies one or more samples of interest as a result of comparing at least one of said electronically captured traits against one of said reference traits, and c. a robotic excision tool coupled to said microprocessor, wherein said microprocessor commands said robotic excision tool to excise at least one sample of interest, wherein said microprocessor commands said robotic excision tool to irrigate said sample media with fluid from a fluid reservoir.

57. An apparatus for automated excision of one or more samples from a sample media, comprising:
   a. a device for electronically capturing one or more traits respectively associated with one or more samples present in a sample media, and
   b. a microprocessor linked to said device for analyzing one or more of said electronically captured traits of one or more of said samples, wherein said microprocessor accesses a database of reference traits and compares at least one electronically captured trait of at least one sample against one of said reference traits in said database of reference traits, wherein the microprocessor identifies one or more samples of interest as a result of comparing at least one of said electronically captured traits against one of said reference traits, and
   c. a robotic excision tool coupled to said microprocessor, wherein said microprocessor commands said robotic excision tool to excise at least one sample of interest, wherein said robotic excision tool has an excision cutting tip that is interchangeable and has means to grip and eject said interchangeable tip and said microprocessor commands said robotic excision tool to grip and eject said interchangeable tip.

58. An apparatus for automated excision of one or more samples from a sample media, comprising:
   a. a device for electronically capturing one or more traits respectively associated with one or more samples present in a sample media, and
   b. a microprocessor linked to said device for analyzing one or more of said electronically captured traits of one or more of said samples, wherein said microprocessor accesses a database of reference traits and compares at least one electronically captured trait of at least one sample against one of said reference traits in said database of reference traits, wherein the microprocessor identifies one or more samples of interest as a result of comparing at least one of said electronically captured traits against one of said reference traits, and
   c. a robotic excision tool coupled to said microprocessor, wherein said microprocessor commands said robotic excision tool to excise at least one sample of interest, wherein said robotic excision tool has an excision cutting tip that is interchangeable and has means to grip and eject said interchangeable tip, wherein said means includes a cylindrical inflatable cuff, an ejection spring, and means to control pressure to and from said inflatable cuff from pressure sources.

59. The apparatus of claim 58, wherein said pressure is fluid pressure.

60. The apparatus of claim 58, wherein said pressure is gas pressure.

61. A method for automating the excision of one or more samples from a sample media, comprising the steps of:
   a. capturing electronically one or more traits respectively associated with one or more samples present in a sample media,
   b. comparing one or more of said captured traits against a database of reference traits,
   c. as a result of step b), selecting a sample of interest from one or more samples present in said sample media,
   d. establishing reference coordinates of said sample of interest,
   e. associating a coring tool with said sample of interest,
   f. automatically excising said sample of interest with said coring tool by reference to said coordinates,
   g. providing a coring tool that is interchangeable, and
   h. gripping said interchangeable coring tool through inflation of a cylindrical inflatable cuff inside the coring tool by liquid or gas pressure.

62. The method of claim 61, further including the step of ejecting said interchangeable tool by releasing said pressure inside said inflatable cuff and applying force to said interchangeable tool with an ejection spring.

* * * * *